United States Patent [19]
Ando et al.

[11] 4,104,145
[45] Aug. 1, 1978

[54] METHOD FOR PRODUCING NITROBENZENE

[75] Inventors: Wataru Ando, Sakura; Ichiro Nakaoka, Machida, both of Japan

[73] Assignee: Kabushiki Kaisha Pollution Preventing Research Laboratory, Tokyo, Japan

[21] Appl. No.: 782,165

[22] Filed: Mar. 28, 1977

[30] Foreign Application Priority Data

Mar. 27, 1976 [JP] Japan .................................. 51-33082

[51] Int. Cl.² .............................................. B01J 1/10
[52] U.S. Cl. .............................................. 204/162 R
[58] Field of Search ..................... 204/162 R; 260/645

[56] References Cited

PUBLICATIONS

Urbanski, Chemistry and Technology of Explosives, vol. 1, The MacMillian Co., New York, 1964, pp. 93 and 134.

*Primary Examiner*—Leland A. Sebastian
*Attorney, Agent, or Firm*—Fitzpatrick, Cella, Harper & Scinto

[57] ABSTRACT

A method for the nitration of benzene by the use of nitrogen dioxide under irradiation of visible ray or ultraviolet ray in the presence of oxygen.

6 Claims, 3 Drawing Figures

INFLUENCE OF OXYGEN IN NITRATION

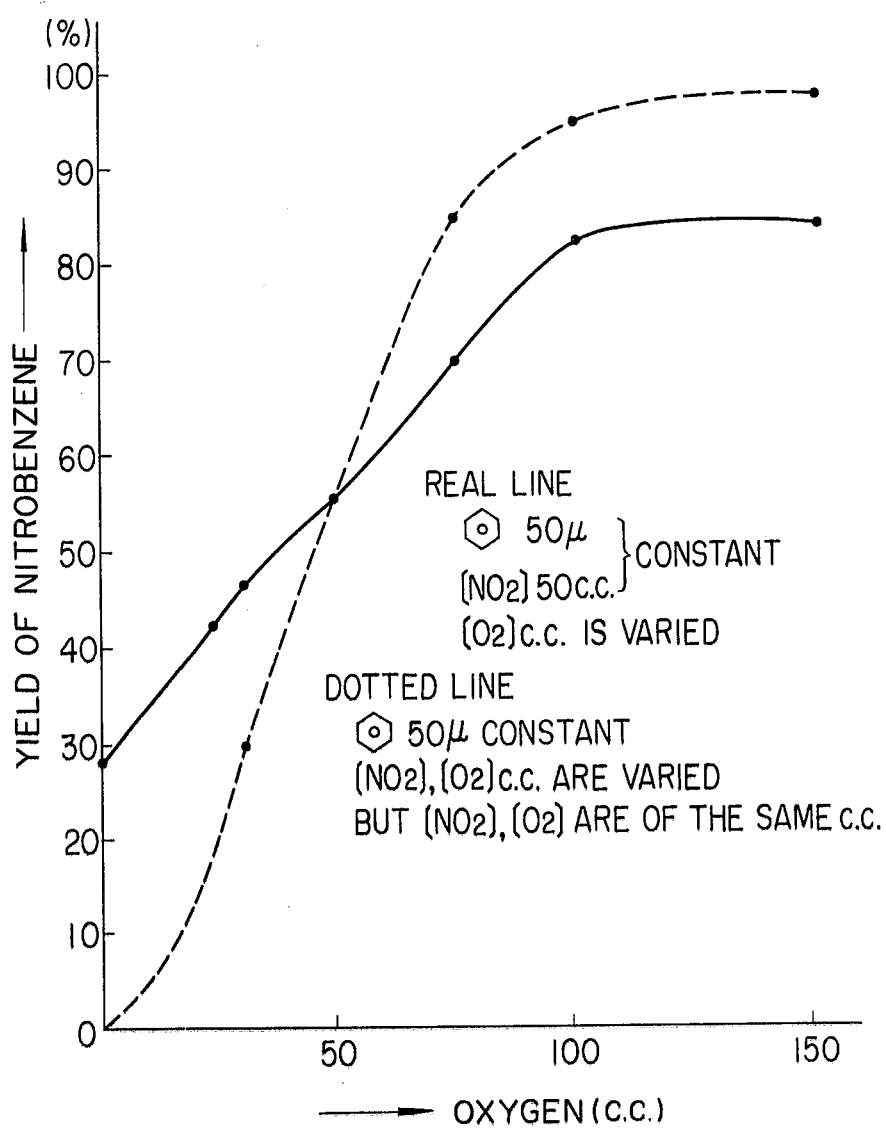

METHOD FOR PRODUCING NITROBENZENE

BACKGROUND OF THE INVENTION a. Field of the Invention

This invention relates to a method for the nitration of benzene by the use of nitrogen dioxide.

b. Description of the Prior Art

In the method of producing nitro compounds, organic compound to which nitro radical being introduced reacts with a nitration reagent or reactant.

The nitration reagent is any one selected from the group of nitric acid (concentrated or diluted), mixed acid (a mixed solution of concentrated nitric acid and concentrated sulfuric acid, a mixed solution of concentrated nitric acid and fuming sulfuric acid, or mixed solution of concentrated nitric acid and acetic anhydride), anhydrous nitric acid $N_2O_5$, organic nitrates (acetyl or benzoyl), inorganic nitrates (mainly, alkali metal salts) and sulfuric acid, or nitryltetrafluoroborate $NO_2^+BF_4^-$ and so forth.

Each nitration reagent is selected suitably depending on the easiness or difficulty of the reaction. The most conventional reagent is nitric acid or a mixed acid in particular, a mixed solution of concentrated nitric acid and concentrated sulfuric acid or fuming sulfuric acid.

In this method, very large amounts of nitric and sulfuric acid are used to the organic starting material so that the mother liquor i.e. the waste acid necessarily remains in fairly large quantities.

The waste acid is separated from resulted nitro compounds, and followed by heating for separation of nitric acid and concentration of sulfuric acid. Furthermore, each acid is concentrated, if desired, for the recovery. This process is commonly known as the waste acid treatment. It is preferable to utilize the waste acid, for example, for decomposing rock phosphate or super phosphate of lime in the fertilizer manufacture, but when there is no utility, the facilities are necessary for the waste acid treatment such as acid reservoirs, pipe line system and pumps for delivering acid and heat furnace for concentration of waste acid and so on. Water pollutions have been caused by the waste acid from the factories depending upon whether or not the arrangement, capacity or maintenance of those facilities are perfect.

Therefore, there is an absolute need for completing the waste acid facility as well as all waste water treatment in the department of nitration process.

No equipment or facility of waste acid treatment is operated economically because of damage i.e. corrosion or errosion thereof and much consumption of fuels. In other words, in view of the waste acid and the additional waste water treatment facilities, the cost of utilities might be negligible.

There have been known various methods for producing nitrobenzene. Those are such as a batch or continuous nitration method of using a mixed solution of nitric and sulfuric acid, azeotropic nitration method (refer to C.A. vol. 84. 1976. 135280w, and Encyclopaedia of Chemical Technology edited by Kirk-Othmer Vol. 9 page 318), and a method of nitration of benzene by the use of a solution of liquid nitrogen dioxide $N_2O_4$ in sulfuric acid (refer to B.67 1363 [1934]) and so forth. In the above method except azeotropic nitration method, it is necessary to perform the waste acid treatment.

The method of nitration of aromatic hydrocarbon by the use of nitrogendioxide or liquid nitrogendioxide $N_2O_4$ had been researched already at the end of the 19th century to the beginning of the 20th century, however, there has been no suitable or valid method of producing nitrobenzene in connection with these methods.

(1) Wieland reported that benzene was allowed to warm with $N_2O_4$ in a sealed tube, resulting in the formation of trinitrobenzene, oxalic acid and carbondioxide. (refer to B. 67 1362 [1934])

(2) Schaarschmidt reported that $NO_2$ gas was introduced into the mixture of benzene and aluminum chloride or ferric chloride to form a complex, followed by hydrolysis to obtain nitrobenzene. (refer to ibid)

(3) Paul Schorigin and A. Toptschien reported that benzene was reacted with nitrogen dioxide under the irradiation or no irradiation of ultraviolet ray in the presence of carbondioxide in such a manner that the nitration reaction was carried out in the molar ratio of benzene to $N_2O_4$ and $CO_2$ being 1 : 4 : 3.6 at the temperature of 25° – 30° C or 55° – 60° C in 2 hours, resulting in a yield of nitrobenzene about 30% based on benzene. That is to say, the conversion rate was about 40 – 50%, the selectivity rate was about 75 – 65%, and the recovery rate of benzene was about 60 – 50%. They said that the influence of ultraviolet ray irradiation on the reaction was not recognized. (refer to B. 67 1363 [1934]). And furthermore, almost the same description are found on page 236, A. B. Topchiev, Izbrannye Trudy Nitrovania Izdatelstovo "Nauka", Moscow, 1965.

(4) Referring to the above Russian literature, on page 265, it was described that liquid $N_2O_4$ was added into benzene in the presence of $BF_3$ to produce nitrobenzene. The reaction may be summarized as follows. 0.5 mol $N_2O_4$ reacted with 1 mol benzene in the presence of $BF_3$ and obtained 22g nitrobenzene in a yield of 18% based on benzene. The reaction temperature rose to 55° – 60° C by adding $N_2O_4$ drop by drop into benzene, because of exothermic reaction, and the reaction mixture was kept at that temperature during 1.5 – 2 hours.

(5) Furthermore, on page 266 of the same literature, the reaction of benzene with $NO_2$ in the presence of catalyst at an elevated temperature of 310° C was described. Nitrobenzene was obtained in the yield of 30.1% in the case of molar ratio of $NO_2$ to benzene 2 : 1, while the yield reached to 83.6% at the same reaction temperature by increasing the molar ratio of $NO_2$ to benzene till 7 : 1.

In addition, referring to Encyclopaedia of Chemical Technology edited by Kirk - Othmer Vol. 9 page 317, mononitro derivatives of aromatic hydrocarbon are prepared, using $HNO_3$ or $NO_2$ (equilibrium mixture of $NO_2$ and $N_2O_4$) in the presence of a catalyst at 130° – 430° C.

(6) On the same page of the above reference, nitration of vapor of benzene has been performed by gaseous nitrogen dioxide in a glow discharge in a Siemens type tube.

Among the products of the reaction were nitrobenzene, m-dinitrophenol and trinitrophenol.

(7) Referring to C.A. Vol. 73 1970 824746, γ-radiation-induced nitration of benzene with liquid $N_2O_4$ at the temperature of 20° C has been described. The major product was nitrobenzene with isomers of dinitrobenzene.

SUMMARY OF THE INVENTION

The present invention provides a method for the nitration of benzene by the use of nitrogen dioxide under irradiation of visible ray or ultraviolet ray in the presence of oxygen.

Regarding the reaction of the present invention, there is no relevant prior arts to the best knowledge of the present inventors, in particular, in connection with the influence of the existence of oxygen on the nitration of benzene in the absence of catalyst under irradiation.

An object of the present invention is to provide a method of nitration whereby no air and water pollution occurs with a very simple and easy waste treatment in a closed system.

That is to say, after the reaction finished excess nitrogen dioxide may be recovered and recycled, and nitrogen oxide may be oxidized to recycle.

A further object of the present invention is to provide a method of nitration capable of coming into batch or continuous operation with a rate of yield of nitrobenzene and safety in the process which is comparable to, or surpassing those of the conventional method.

A further object of the present invention is to realize an effective utilization of $NO_x$ which is a harmful component in the combustion waste gas from boiler or heating furnace in the power station, iron foundry and petrochemical factory and so on.

That is to say, $NO_x$ may be oxidized by the known method to convert nitrogen dioxide which may be liquified to $N_2O_4$ being stored and used as the source of nitrogen dioxide.

Or else, as the source of nitrogen dioxide, NO gas produced from a nitric acid producing plant operating by catalytic ammonia oxidation method may be used.

$NO_2$ may be obtained from NO in the same manner described above.

The foregoing object, other objects and the reaction to take place in the method of the present invention will become more apparent and understandable from the following detailed explanation of the present invention, when read in connection with several preferred examples thereof.

BRIEF EXPLANATION OF THE DRAWING

The data of tables I and II were indicated diagrammatically for the purpose of illustrating the influence of oxygen or the nitration of benzene with nitrogendioxide of the present invention. Ordinate indicates the yield of nitrobenzene and abscissa indicates also the quantity of oxygen.

DESCRIPTION OF THE PREFERRED EMBODIMENT (1) The mechanism of the conventional nitration of benzene in liquid phase is indicated as follows.

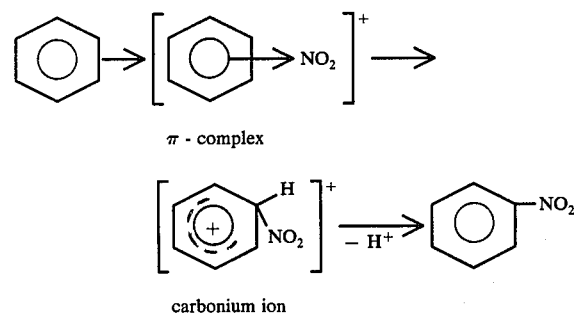

π - complex carbonium ion wherein electrophilic nitronium cation attacks benzene ring and the reaction proceeds with deproton (removal of proton) and completes.

(a) As nitric acid is a nitration reagent, $NO_2^+$ is formed as follows:

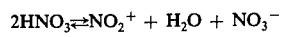

$$2HNO_3 \rightleftharpoons NO_2^+ + H_2O + NO_3^-$$

(b) As mixed acid is a nitration reagent, $NO_2^+$ is formed as follows:

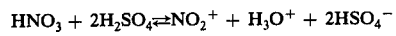

$$HNO_3 + 2H_2SO_4 \rightleftharpoons NO_2^+ + H_3O^+ + 2HSO_4^-$$

(2) As nitryltetrafluoroborate is a nitration reagent, the reaction proceeds as follows:

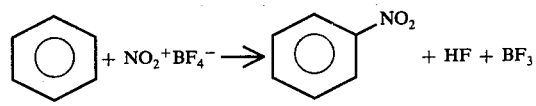

(3) The mechanism of the nitration of benzene with the use of $NO_2$ in vapor phase has been considered as the radical reaction.

Now, the hypothetical mechanism of the nitration of the present invention will be shown wherein the situation of benzene is in liquid phase and/or vapor phase and the situation of nitrogen dioxide is in vapor phase.

The reaction is regarded as chain mechanism.

Equation (1): $NO_2 \rightleftharpoons NO\cdot + O\cdot$
Equation (2): $N_2O_4 \rightleftharpoons NO_2^* + NO_2^*$
* is (+) or (.)

Equation (3):

$$NO\cdot + O_2 \rightleftharpoons ON-O-O\cdot \xrightarrow{NO\cdot} ON-O-O-NO\cdot$$
$$\downarrow$$
$$2NO_2^*$$

Equation (4):

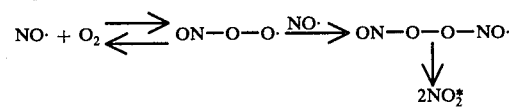

active complex

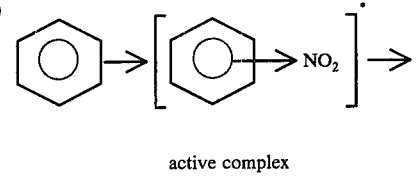

Equation (5):

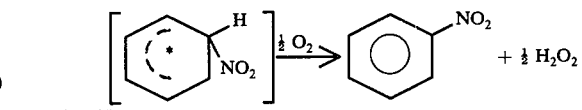

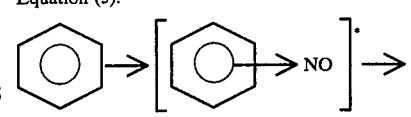

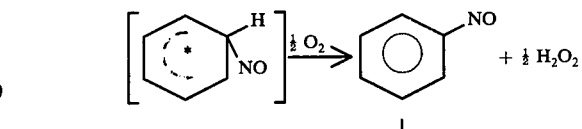

* is (+) or (*)

Equation (6):

-continued

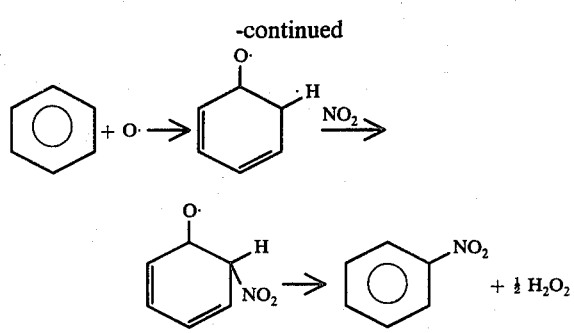

Side Reactions

Equation (7): $H_2O_2 \rightarrow H_2O + O$.
Equation (8): $O. + O_2 \rightarrow O_3$
Equation (9): $O_3 \rightarrow O_2 + O$.
Equation (10): $O. + O_3 \rightarrow 2O_2$ As shown above, in the nitration of the present invention the existence of oxygen is the absolute and indispensable requisite to be noted.

In summary of the foregoing, the characteristic feature of the present invention consists in the method of performing the nitration of benzene by the use of nitrogen oxide under irradiation of visible or ultraviolet ray in the presence of oxygen.

In order to enable those persons skilled in the art to readily perform the present invention into practice, the following preferred examples are presented.

It should, however, be noted that these examples are merely illustrative and not restrictive, and that any change and modification may be made by those skilled in the art in respect of the various reaction conditions as mentioned in the foregoing without departing from the spirit and scope of the present invention as set forth in the appended claims.

Hereinafter, the embodiments will be shown.

Method Of Experiment 400 ml Pyrex glass tube was degassed in which benzene, nitrogendioxide and oxygen were introduced and closed. The reaction mixture was irradiated by means of high pressure mercury lamp at the temperature of 20° - 25° C in 2 hours.

The resulted product was extracted with chloroform, followed directly by quantitative analysis by means of gaschromatography.

Results Of Experiment (1) The following data were obtained under a condition at which the quantities of benzene and nitrogen dioxide were constant, i.e. 50μ and 50 cc respectively. But oxygen quantity was variable.

Table I

| No. | 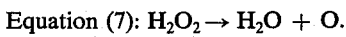 | $NO_2$ | $O_2$ | yield of nitrobenzene |
|---|---|---|---|---|
| 1 | 50 μ | — | — | 0 % |
| 2 | 50 μ | 50 cc | — | 28 % |
| 3 | 50 μ | 50 cc | 25 cc | 42 % |
| 4 | 50 μ | 50 cc | 30 cc | 47 % |
| 5 | 50 μ | 50 cc | 50 cc | 55 % |
| 6 | 50 μ | 50 cc | 75 cc | 70 % |
| 7 | 50 μ | 50 cc | 100 cc | 83 % |
| 8 | 50 μ | 50 cc | 150 cc | 85 % |

(2) The following data were obtained under a condition at which the quantity of benzene was constant, but the quantities of nitrogen dioxide and oxygen were variable and each amount of oxygen and nitrogen dioxide was the same.

Table II

| No. | 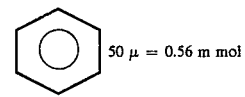 | $NO_2$ | $O_2$ | yield of nitrobenzene |
|---|---|---|---|---|
| 1 | 50 μ | — | — | 0 % |
| 2 | 50 μ | 15 cc | 15 cc | 5 % |
| 3 | 50 μ | 25 cc | 25 cc | 17 % |
| 4 | 50 μ | 30 cc | 30 cc | 30 % |
| 5 | 50 μ | 50 cc | 50 cc | 55 % |
| 6 | 50 μ | 75 cc | 75 cc | 85 % |
| 7 | 50 μ | 100 cc | 100 cc | 95 % |
| 8 | 50 μ | 150 cc | 150 cc | 98 % |

Note:

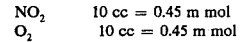 50 μ = 0.56 m mol $NO_2$ 10 cc = 0.45 m mol
$O_2$ 10 cc = 0.45 m mol

In the method of prior application, the ratio of benzene, nitrogen dioxide and oxygen were 1 : 2 : 4. The reaction was carried out at the temperature of 20° - 25° C in 9 hours. Nitrobenzene was obtained in a yield of about 30% based on benzene.

On the other hand, in the method of the present invention as shown obviously from tables I and II and the figure, the relative ratio of benzene, nitrogen dioxide and oxygen was varied.

Particularly, the molar ratio of benzene to nitrogendioxide was 1 : 4 or more than 4 and the molar ratio of $NO_2$ to $O_2$ was 1 : 1 or more than 1. The reaction was carried out at the temperature of 20° - 25° C in 2 hours. Nitrobenzene was obtained in a yield of 55% (minimum) - 85% (maximum) based on benzene in the case of experiment (1), while in a yield of 55% (minimum) - 98% (maximum) based on benzene in the case of experiment (2), respectively.

It is considered that the increase of the yield depends on the following reasons.

Existence of excess oxygen is very effective in the regeneration of NO. to $NO_2^*$ and recycle thereof. [refer to Eq. (3)] When the reaction system is always rich in the amount of $NO_2^*$ and the more the probability of collision of molecules of nitrogendioxide $NO_2^*$ and benzene is increased, the more the reaction is accelerated. Then, referring to Eq. (4) - (6), and Eq. (7) - (10) of the mechanism, it is obvious that the existence of oxygen is indispensable in the method of the present invention. The reaction proceeds preferably in the presence of much amount of oxygen.

From the foregoing description, the method of the present invention is not the same method of the prior application, but is an advanced method.

Furthermore, in the method of Toptschiev benzene reacted with nitrogendioxide to produce nitrobenzene under irradiation or no irradiation of ultraviolet ray in the absence of oxygen in the molar ratio of benzene to $N_2O_4$ 1 : 4 i.e. in the molar ratio of benzene to $NO_2$ 1 : 8. The reaction time and temperature were almost similar to those of the method of the present invention, but nitrobenzene was obtained about in a yield of 30% based on benzene being about one third of the maximum yield of the present invention.

In the conventional method of nitration of benzene with mixed acid in a batch reactor, the yield of nitrobenzene is in 98 – 99% based on benzene being almost similar to the maximum yield of the present invention.

The reaction time, however, is about 5 – 6 hours and a long settling time is necessary to separate nitrobenzene from the mother liquor i.e. the waste acid. A long additional time is necessary to wash and refine crude nitrobenzene so that the total time of process after nitration is over 10 hours.

Therefore, the overall process time of the method of this invention might be reduced, because the separation, washing and purification might be performed easily. In particular, there is no need for treating waste acid (recovery of sulfuric acid), and is no air pollution problem because of possibility of operating the process in a closed system.

From the foregoing descriptions, it is obvious that the method of the present invention is a method for producing nitrobenzene in a high yield with no pollution as compared with the conventional methods known or applied in practice. It is possible to say that the method of the present invention might be operated in a continuous process as well as in a batch process.

What we claim is:

1. In the method for reacting benzene with nitrogendioxide to produce nitrobenzene under irradiation of visible ray or ultraviolet ray in the presence of oxygen characterized in that excess nitrogendioxide and excess oxygen are added to benzene, respectively.

2. The method as defined in claim 1 which comprises the molar ratio of benzene to nitrogendioxide being 1 : 4 or more than 4.

3. The method as defined in claim 1 which comprises the molar ratio of benzene to nitrogenoxide being 1 : 4 or less than 4.

4. The method as defined in claim 1 which comprises the molar ratio of nitrogendioxide to oxygen being 1 : 1 or more than 1.

5. The method as defined in claim 1 which comprises the molar ratio of nitrogenoxide to oxygen being 1 : 1 or less than 1.

6. Method for producing nitrobenzene comprising: reacting benzene with nitrogen dioxide and oxygen under visible or ultraviolet irradiation and maintaining the molar ratio of benzene to nitrogen dioxide at least 1 : 4 and the molar ratio of nitrogen dioxide to oxygen at least 1 : 1 during said reaction.

* * * * *